US008516642B1

(12) United States Patent
Farahat (10) Patent No.: US 8,516,642 B1
(45) Date of Patent: Aug. 27, 2013

(54) CURVED-HEAD ELECTRIC TOOTHBRUSH

(75) Inventor: Ashraf Mohamed Samir Farahat, Kelowna (CA)

(73) Assignee: King Fahd University of Petroleum and Minerals, Dhahran (SA)

( * ) Notice: Subject to any disclaimer, the term of this patent is extended or adjusted under 35 U.S.C. 154(b) by 33 days.

(21) Appl. No.: 13/401,668

(22) Filed: Feb. 21, 2012

(51) Int. Cl.
*A61C 17/22* (2006.01)
(52) U.S. Cl.
USPC .................................. 15/22.1; 15/28
(58) Field of Classification Search
USPC .................................... 15/22.1, 28
See application file for complete search history.

(56) References Cited

U.S. PATENT DOCUMENTS

| | | | |
|---|---|---|---|
| 2,583,886 A | 1/1952 | Schlegel | |
| 2,628,377 A | 2/1953 | Cockriel | |
| 4,156,620 A * | 5/1979 | Clemens | ........................... 134/6 |
| 4,224,710 A | 9/1980 | Solow | |
| 4,382,309 A | 5/1983 | Collis | |
| 5,177,827 A | 1/1993 | Ellison | |
| 5,337,435 A | 8/1994 | Krasner et al. | |
| 5,428,855 A | 7/1995 | Li | |
| 6,343,396 B1 | 2/2002 | Simovitz et al. | |
| 7,020,925 B1 * | 4/2006 | Gitelis | ........................... 15/22.1 |
| 7,082,638 B2 | 8/2006 | Koh | |
| 2011/0067194 A1 | 3/2011 | Al-Qaffas | |

FOREIGN PATENT DOCUMENTS

EP    488 971 A2    6/1992

* cited by examiner

*Primary Examiner* — Mark Spisich
*Assistant Examiner* — Andrew A Horton
(74) *Attorney, Agent, or Firm* — Richard C. Litman (57) ABSTRACT

The curved-head electric toothbrush includes an elongate housing having a drive assembly contained therein. The housing provides a handle portion and a tapering section that holds a curved brush mount. The curved brush mount has a plurality of rotatable brush units mounted thereon. The brush mount is shaped to conform to the curved row of teeth of a user's mouth. The drive assembly drives one of the brush units, and the rest of the brush units are driven by the driving brush unit so that adjacent brush units rotate in opposite directions. Each brush unit includes curved, outer bristles and straight, inner bristles, the former for cleaning the outer side surfaces and the latter for the top surface of teeth. In use, the curved-head electric toothbrush simultaneously cleans substantially the whole row of teeth with minimal manual manipulation.

9 Claims, 7 Drawing Sheets

CURVED-HEAD ELECTRIC TOOTHBRUSH

BACKGROUND OF THE INVENTION

1. Field of the Invention

The present invention relates to dental hygiene devices, and particularly to a curved-head electric toothbrush that insures proper cleaning of all teeth in an efficient manner.

2. Description of the Related Art

Development of oral hygiene and dental care is very important in a young person's life. If proper care is exercised, their teeth can last a lifetime. Improper care leads to cavities and other ailments that can dramatically reduce the life of one's teeth.

One hindrance that leads to bad habits is the typical short attention span and exuberant energy of youngsters. When brushing, one must reach all areas of the teeth for a thorough clean, which requires diligence and attention. Unfortunately, a child may not have the patience or willingness to expend much effort for such an activity.

Currently, electric or automatic toothbrushes have become very popular and help make brushing a relatively fast and efficient affair. Electric toothbrushes usually clean one's teeth better than conventional manual toothbrushes. Moreover, minimal physical effort is required to brush one's teeth, since the majority of the cleaning is accomplished by moving brushes. While such electric toothbrushes provide great time-saving benefits and convenience, they still suffer from similar drawbacks of manual brushes. More specifically, the design of the brush head for most toothbrushes limits how many teeth can be cleaned at a time. Thus, the user must still manipulate and spend adequate time at each point of reach for a complete clean.

Thus, a curved-head electric toothbrush solving the aforementioned problems is desired.

SUMMARY OF THE INVENTION

The curved-head electric toothbrush includes an elongate housing having a drive assembly contained therein. The housing has a handle portion and a tapering section that holds a curved brush mount. The curved brush mount has a plurality of rotatable brush units mounted thereon, and the brush mount is shaped to conform to the curved row of teeth of a user's mouth. The drive assembly drives one of the brush units, and the rest of the brush units are driven by the driving brush unit so that adjacent brush units rotate in opposite directions. Each brush unit includes curved outer bristles and straight inner bristles, the former for cleaning the outer side surfaces and the latter for the top surface of teeth. In use, the curved-head electric toothbrush simultaneously cleans substantially the whole row of teeth with minimal manual manipulation.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
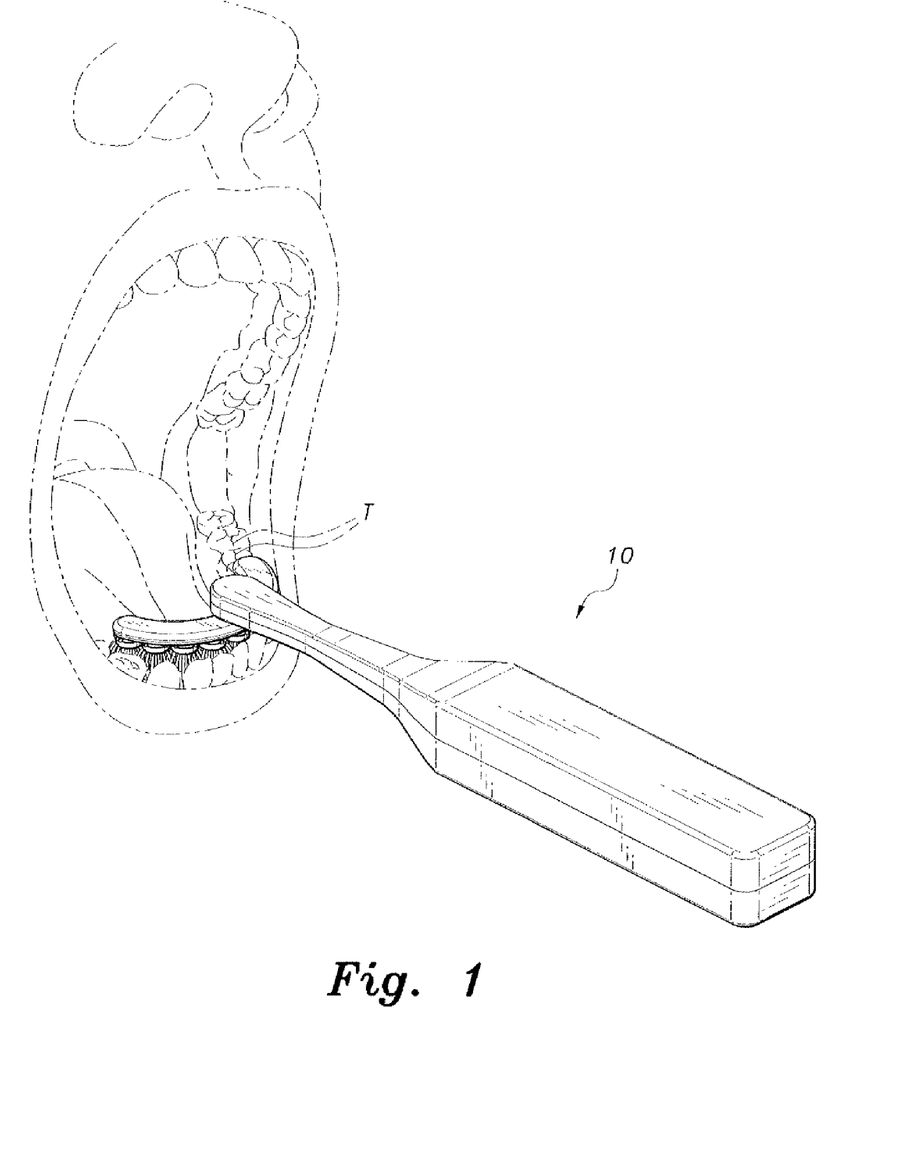
FIG. 1 is an environmental, perspective view of a curved-head electric toothbrush according to the present invention.
Figure 2:
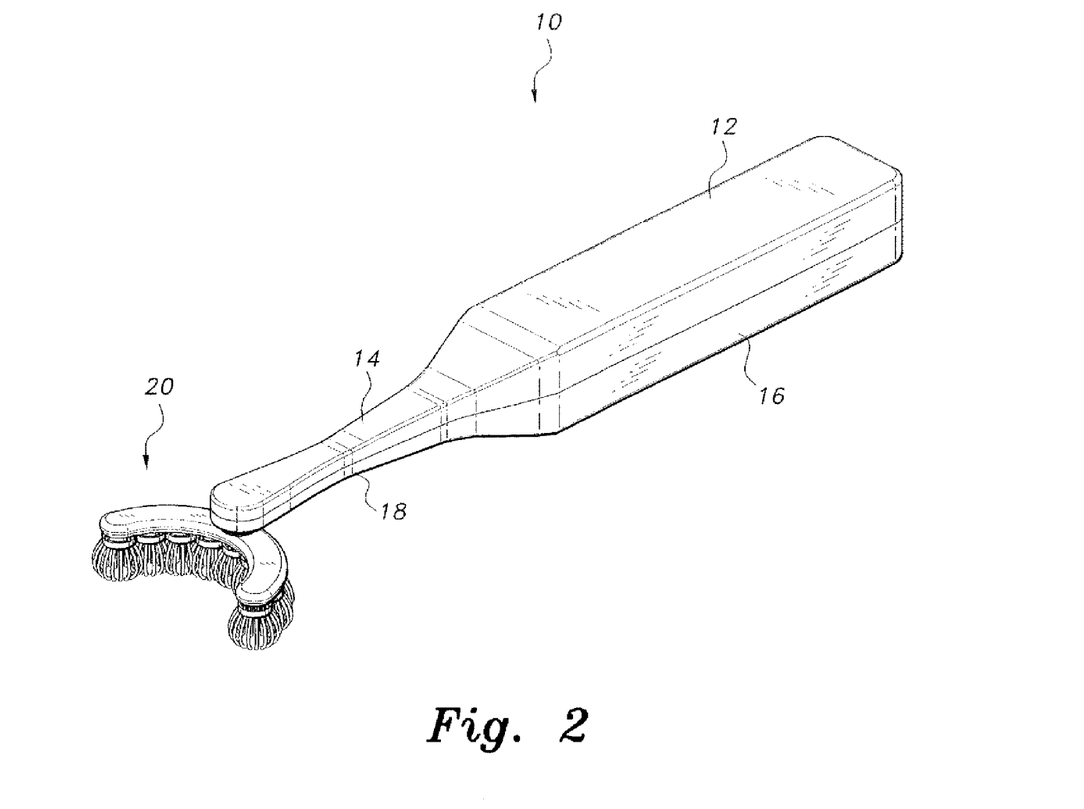
FIG. 2 is a perspective view of the curved-head electric toothbrush of FIG. 1.
Figure 3:
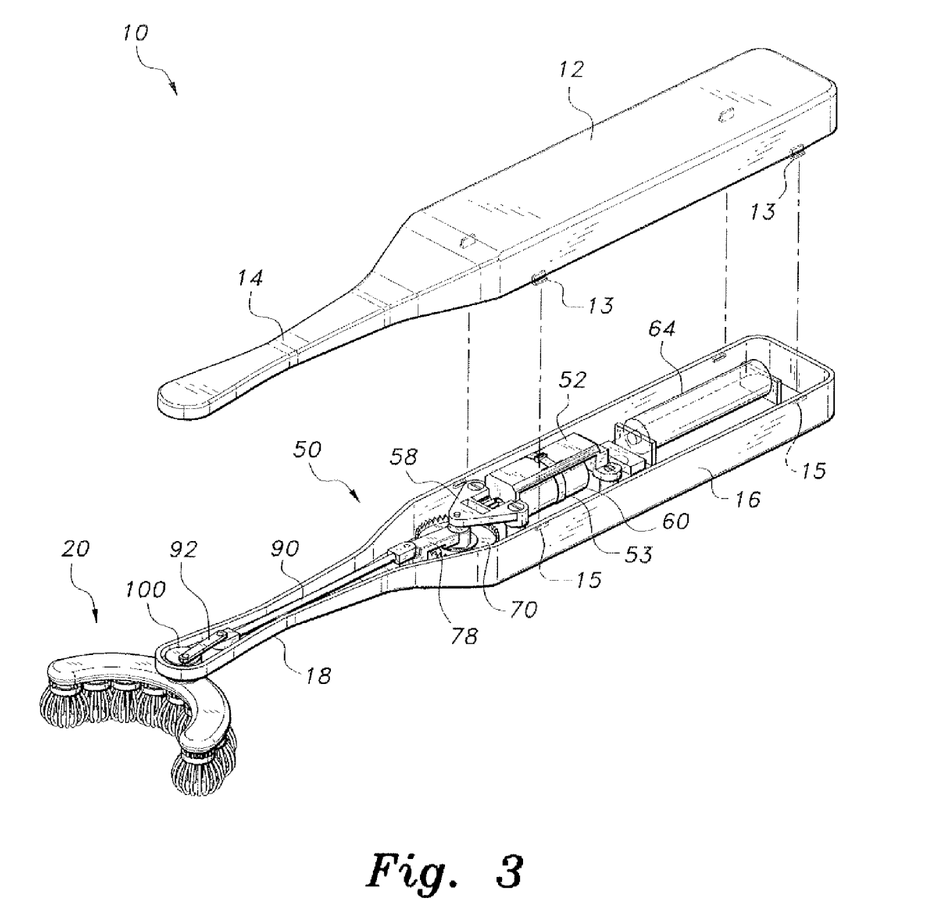
FIG. 3 is a partially exploded view of the curved-head electric toothbrush of FIG. 2.

The curved-head electric toothbrush, generally referred to by the reference number 10 in the drawings, provides convenient and timesaving cleaning of substantially all of a row of teeth T in a single cleaning application. As shown in FIGS. 1-3, the curved-head electric toothbrush 10 includes an elongate housing having an upper, removable casing or cover 12 and a lower, base or casing 16. The lower casing 16 defines a compartment that houses all of the components for operating the curved head electric toothbrush 10, while the upper casing 12 covers and protects the components within the lower casing 16. The housing is substantially rectangular for about half of its length and tapers to an elongate, relatively narrow upper neck portion 14 and lower neck portion 18, the upper and lower neck portions 14, 18 defining the neck of the housing and extending the remainder of the length thereof. This overall shape provides a handle or gripping section at the rectangular portion, and the elongate neck provides an extension for unobstructed insertion and manipulation of the curved brush head 20 during use. The neck also encases some of the driving components for the curved brush head 20, which will be further detailed below.

The upper casing 12 is selectively removable from the lower casing 16 to gain access to the interior components for routine maintenance and/or change of batteries. To facilitate detachable mounting of the upper casing 12, the upper casing 12 can be provided with interference tabs 13 that mate with corresponding protrusions or extensions 15 in the lower casing 16. Other types of fasteners, such as clips, can also be used and placed at any desired or required locations along the housing. The housing is preferably constructed from durable plastic that can withstand daily use. Other materials, such as lightweight metals, composites and/or combinations thereof, are viable alternatives. Moreover, the seam between the upper and lower casings 12, 16 can be sealed by a seal ring in order to waterproof the curved-head electric toothbrush 10 and prevent inadvertent damage to the interior components.

The curved-head electric toothbrush 10 includes an arcuate or curved brush head 20 disposed at the terminal or distal end of the neck portions 14, 18. The curved brush head 20 is configured to facilitate brushing of a plurality of teeth or a whole row of teeth at one time. As shown in FIGS. 1-4 and 7A, the curved brush head 20 includes an arcuate or curved brush mount or frame 22. The curved brush mount 22 is substantially C-shaped or U-shaped to conform to the shape of the user's row of teeth T, having a bight and legs extending from the bight. A plurality of mounting slots or recesses 24 are formed on the bottom of the brush mount 22. The mounting slots 24 accommodate insertion of brush units 30, which will be further discussed below. The top of the brush mount 22 includes a centrally disposed, disc-shaped mounting boss 26 at the bight of the U-shape for attaching the brush mount 22 to the drive assembly 50 of the curved-head electric toothbrush 10. The mounting boss 26 includes a drive bore 28 to accommodate a drive shaft from the drive assembly 50 and a pair of spaced stabilizing pegs 27. When mounted, the stabilizing pegs 27 are inserted into corresponding stabilizing bores 17 formed at the distal end of the lower neck portion 18, which fixes attachment of the brush mount 22 to the neck of the housing and prevents unwanted movement thereof during use.

The plurality of brush units 30 are rotatably mounted to the underside of the brush mount 22 and configured so that upon driving rotation of one brush unit 30, the driving brush unit 30 rotates the rest of the brush units 30. As shown in FIGS. 1-4, 8A and 9, each brush unit 30 includes a circular spur gear 32 detachably mounted to a brush 40. Each spur gear 32 includes two sets of gear teeth 34 formed on diametrically opposed sectors of the circular spur gear 32. The remaining sectors or sections 37 are smooth, thus forming a discontinuity in the arrangement of the gear teeth 34. During operation, this configuration of spur gears 32 allows for a very forgiving driving engagement between adjacent spur gears 32 without compromising rotational movement of the brush units 30.

Figure 8A:
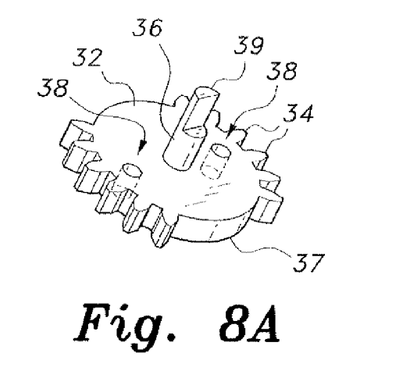
FIG. 8A is a perspective view of a spur gear for a curved-head electric toothbrush according to the present invention.

Each spur gear 32 also includes an axially extending mounting shaft or rod 36 for mounting the spur gear 32 to the mounting slot 24. At least the driving spur gear 32 can include the mounting shaft 36 with a notched extension 39 as shown in FIG. 8A. The notched extension 39 can be semi-circular in cross section so that the notched extension 39 can be mated to the camshaft 104 from the drive assembly 50 and be rotated thereby. The driven spur gears 32 can include similarly constructed mounting shafts 36 for ease of manufacture, or they may be formed without the notched extension 39. Each spur gear 32 further includes diametrically opposed mounting slots or bores 38 for mounting the brush 40 thereon on the opposite side of the spur gear 32 from the mounting shaft 36. To insure that the mounting shafts 36 do not slip from the respective mounting bore 24, each shaft 36 can include an annular, outer protrusion 35 that mates with an inner, circular groove 25 inside the mounting bore 24.

Figure 4:
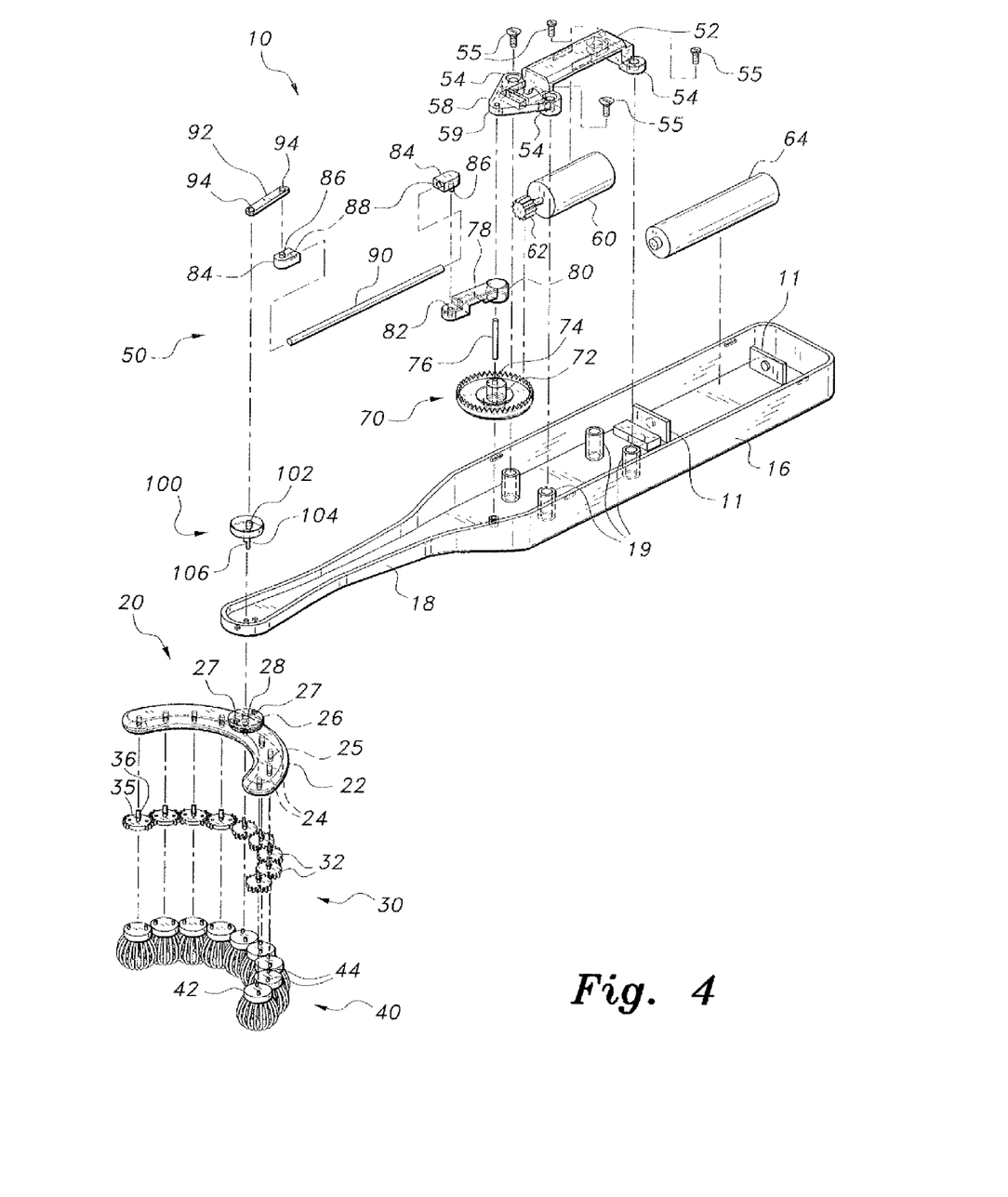
FIG. 4 is an exploded view of the curved-head electric toothbrush of FIG. 1.
Figure 5:
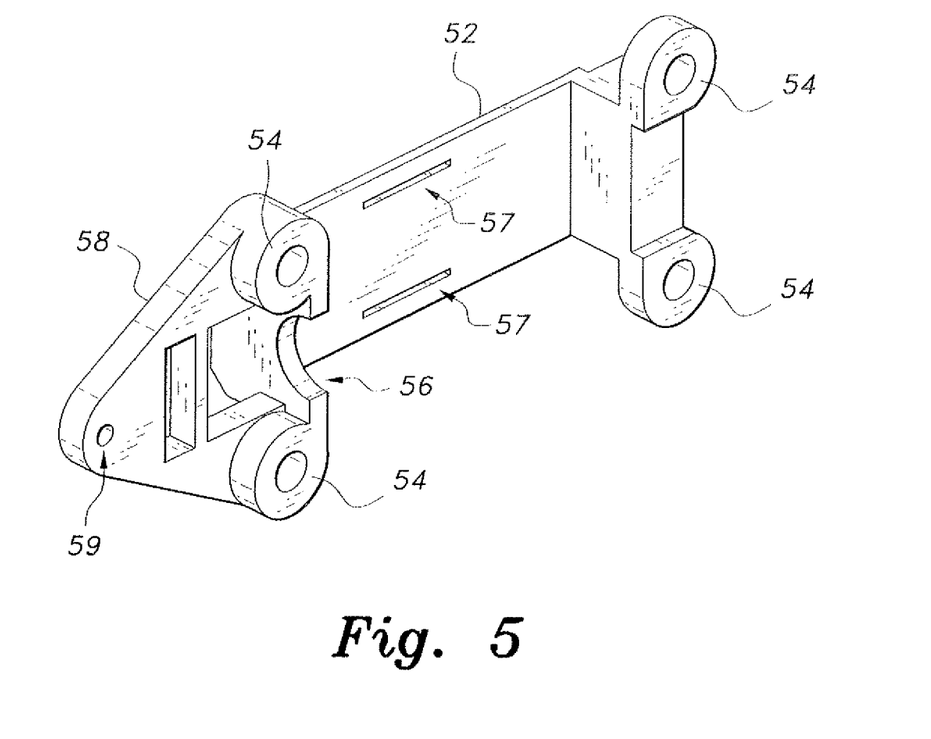
FIG. 5 is a perspective view of a motor bracket for a curved-head electric toothbrush according to the present invention.
Figure 9:
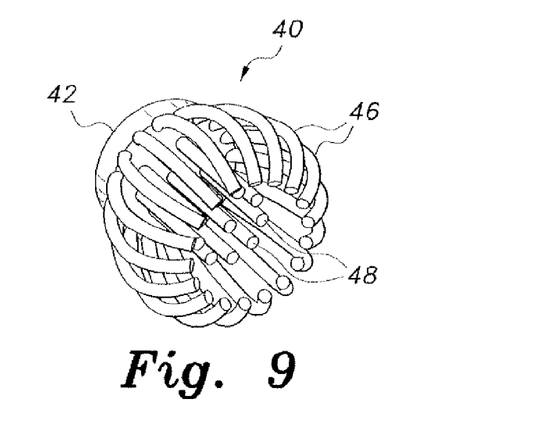
FIG. 9 is a perspective view of a brush for a curved-head electric toothbrush according to the present invention.

Referring to FIGS. 4 and 9, each brush 40 includes a circular mounting collar or boss 42 with integral mounting pegs 44 arranged on diametrically opposed sides on the top of the mounting collar 42. The pegs 44 are configured to be insertably mounted in corresponding mounting bores 38 on the respective spur gear 32.

The opposite side of the mounting boss 42 includes an arrangement of bristles extending therefrom. These bristles are configured to provide thorough cleaning of all sides of the teeth T. As shown in FIG. 9, the arrangement of bristles includes a plurality of outer, curved bristles 46 and a plurality of inner, straight bristles 48. The outer, curved bristles 46 form a spherical cage around the inner, straight bristles 48. The straight bristles 48 also do not extend as far as the outer bristles 46, i.e., the straight bristles 48 are shorter than the curved bristles 46. During use, rotation of the brush 40 allows the outer bristles 46 to contact and clean the outer sides of the teeth T while the shorter straight bristles 48 contact the top of the teeth T to clean the tooth. The curved shape of the outer bristles 46 also allows for cleaning of the space between adjacent teeth T, i.e., the shape provides simultaneous floss-like cleaning of the teeth T.

As mentioned previously, rotation of one driving brush unit 30 simultaneously rotates the remaining brush units 30. In reference to FIG. 4, the center brush unit 30 is directly attached to the drive assembly 50 to be rotated thereby. The remaining brush units 30 are mounted and arranged so that adjacent spur gears 32 are engaged with each other. With this arrangement, rotation of the center spur gear 32 rotates adjacent driven spur gears 32 in opposite directions. This type of rotational movement of the adjacent brush units 30 helps to insure thorough cleaning of the teeth T, compared to having all the brush units 30 rotating in the same direction.

Figure 7A:
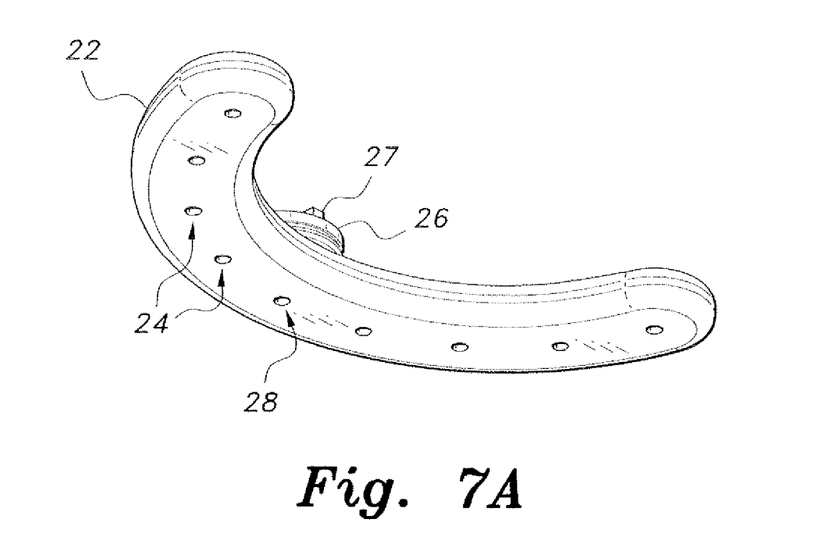
FIG. 7A is a perspective view of a curved brush mount for a curved-head electric toothbrush according to the present invention.
Figure 7B:
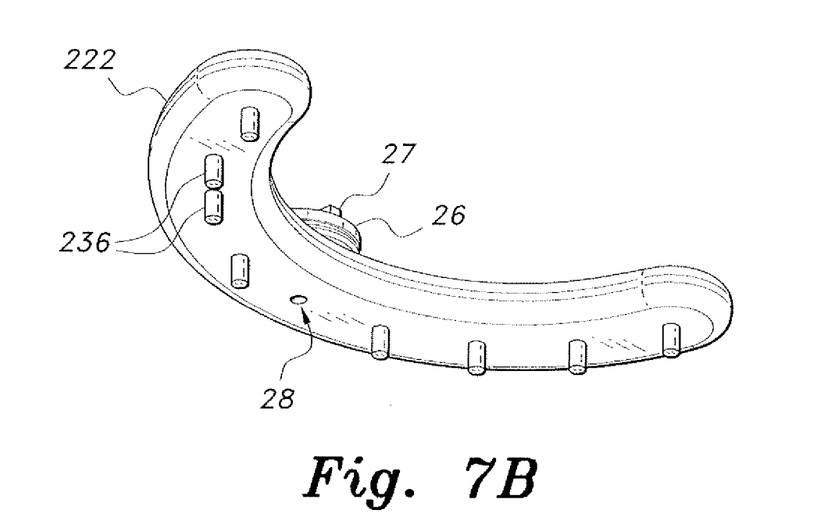
FIG. 7B is a perspective view of an alternative embodiment of a curved brush mount for a curved-head electric toothbrush according to the present invention.
Figure 8B:
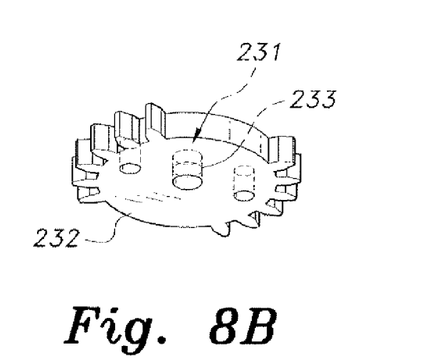
FIG. 8B is a perspective view of an alternative embodiment of a spur gear for a curved-head electric toothbrush according to the present invention.
Figure 8C:
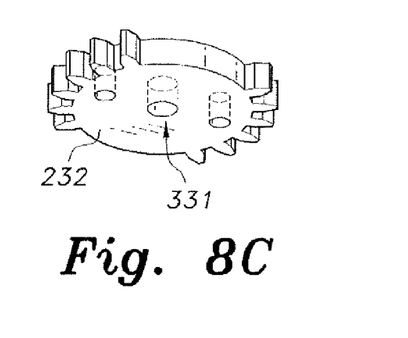
FIG. 8C is a perspective view of another embodiment of a spur gear for a curved-head electric toothbrush according to the present invention.

Alternative configurations for the spur gears 32 are exemplarily shown in FIGS. 8B and 8C for use with the alternative curved brush mount 222 shown in FIG. 7B. As shown, the alternative brush mount 222 is substantially the same as the previous brush mount 22, except that the brush mount 222 includes integral mounting pegs 236. The mounting pegs 236 can be used to mount alternative driven spur gears 232, shown in FIG. 8B, or spur gear 332, shown in FIG. 8C. The spur gears 232 and 332 are similar to spur gear 32. However, spur gear 232 includes a central mounting bore 231 having an inner, circular groove 233 that mates with a corresponding protrusion or lip in mounting peg 236. Alternatively, the spur gear 332 includes a smooth mounting bore 331 that forms a pressure fit with the pegs 236. With both alternative embodiments of the spur gears, the mounting peg 236 can be permanently attached to the mounting boss 42 on the brush 40 via adhesives and the like.

To drive the brush units 30, the curved-head electric toothbrush 10 includes a drive assembly 50 disposed in the lower casing 16. As shown in FIGS. 3-6, the drive assembly includes a motor bracket 52 for securely holding a motor 60 within the lower casing 16. The motor bracket 52 is substantially U-shaped with four mounting bosses 54 disposed at the corners thereof. The motor bracket 52 is secured to the lower casing 16 by fasteners, such as screws 55, inserted through bores in the mounting bosses 54 and threaded into corresponding lower mounting bosses 19.

The motor 60 is preferably an electric motor having a pinion 62 extending from one side of the motor 60. The power for driving the motor 60 is provided by a power source, such as a battery 64. The battery 64 is mounted between terminals 11, and the battery 64 can be disposable or rechargeable.

While the motor 60 can be configured to be secure between the lower mounting bosses 19 and the motor bracket 52, additional measures can be incorporated by utilizing a strap threaded through slots 57 to secure the motor 60 to the motor bracket 52. The bottom of the motor bracket 52 includes a semi-circular cutout 56 to provide clearance for the pinion 62.

The pinion 62 drives a crown gear 70 rotatably mounted to the bottom of the lower casing 16 by a pin 76. The pin 76 defines the axis of rotation for the crown gear 70. The pin 76 is secured at one end to a boss at the bottom of the casing 16, and the other end is secured to a triangular head portion 58 of the motor bracket 52 through a bore 59.

The crown gear 70 includes an eccentric drive boss 72 having a through bore 74. The pin 76 extends through the bore 74. The eccentric drive boss 72 helps convert rotation motion into linear movement. An elongate transmission arm 78 includes a rounded end having a bore 80. The transmission arm 78 is rotatably mounted to the eccentric drive boss 72 via the bore 80. Thus, as the crown gear 70 rotates about the axis defined by the pin 76, the eccentric boss 72 drives the transmission arm 78 in an eccentric reciprocating manner.

The drive assembly 50 also includes an elongate transmission shaft 90. The transmission shaft 90 lies within the neck of the housing. A connector 84 is attached to each end of the transmission shaft 90 via a mounting recess 88 in each connector 84. Each connector 84 also includes a mounting peg 86. When assembled, one end of the transmission shaft 90 is rotatably connected to the opposite end of the transmission arm 78 through the mounting bore 82 via the respective mounting peg 86, and the other end of the transmission shaft 90 is rotatably connected to a crank arm 92 via the other mounting peg 86 through one of the bores 94 in the crank arm 92. The crank arm 92 is, in turn, rotatably attached to a cam 100.

Figure 6:
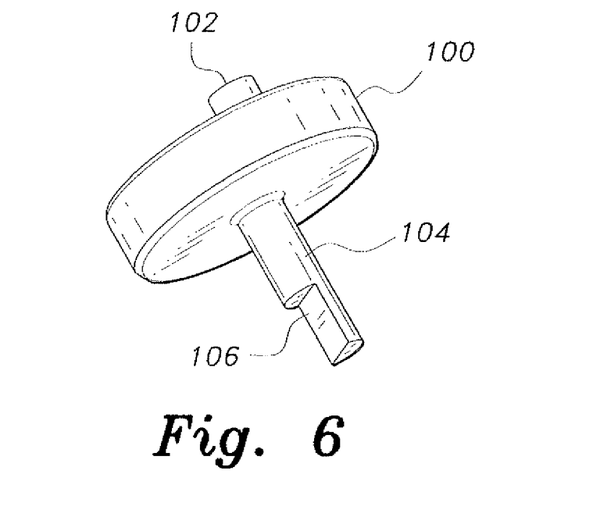
FIG. 6 is a perspective view of a cam for a curved-head electric toothbrush according to the present invention.

As shown in FIGS. 4 and 6, the cam 100 includes a disc-shaped body having an eccentric mounting peg 102 disposed on the top side of the main body. The mounting peg 102 connects the cam 100 to the other end of the crank arm 92 via the bore 94, and the mounting peg 102 is eccentric by being disposed offset from the axis of rotation of the camshaft 100. The bottom of the main body includes an axially extending camshaft 104 having a notched extension 106. The camshaft 104 is configured to extend through the lower casing 16 into the drive bore 28 of the brush mount 22 to thereby mate with a corresponding notched extension 39 on the driving spur gear 32. Thus mated with the flat surfaces of the notched extensions 39, 106, rotation of the camshaft 100 facilitates rotation of the spur gears 32.

To summarize, with all the components of the drive assembly 50 assembled, activation of the motor 60 rotates the pinion 62. The pinion 62 drives the crown gear 70 causing the transmission arm 78 and the transmission shaft 90 to reciprocate in an eccentric manner due to the eccentric connection between the transmission arm 78 and the eccentric drive boss 72. The eccentric reciprocation of the transmission shaft 90 drives the crank arm 92, which, in turn, rotates the cam 100. Rotation of the cam 100 rotates the spur gears 32, which facilitates the cleaning brushing action of the brushing units 30.

Thus, it can be seen that the curved-head electric toothbrush 10 provides a relatively simple and efficient solution for simultaneous brushing of a row of teeth. The drive assembly 50 drives a single gear in one brush unit 30, and the geared connection between all the brush units 30 allows simultaneous rotation of all from one. The configuration of the brush 40 also allows for a complete and thorough cleaning of the teeth with minimal manual manipulation of the curved-head electric toothbrush 10. The curved-head electric toothbrush 10 is ideal for children, but it can also be used by others with simple resizing and/or number of brush units 30 included thereby.

It is to be understood that the present invention is not limited to the embodiments described above, but encompasses any and all embodiments within the scope of the following claims.

I claim:

1. An curved-head electric toothbrush, comprising:
   an elongate housing having a handle portion and a neck portion, the housing having a selectively removable upper easing and a lower casing;
   a curved brush mount extending substantially perpendicular to the neck portion, the curved brush mount being dimensioned and configured to fit substantially a whole curved row of teeth in a user's mouth, the curved brush mount defining a plane;
   a plurality of brush units including a single drive brush unit and a plurality of driven brush units connected to the drive brush unit, the brush units being rotatably mounted to the curved brush mount, each of the brush units having a brush rotating about an axis perpendicular to the plane of the curved brush mount; and
   a drive assembly disposed inside the housing, the drive assembly rotating the drive brush unit, thereby rotating the remaining brush units.

2. The curved-head electric toothbrush according to claim 1, wherein said curved brush mount has a top surface and a bottom surface, said brush mount having a mounting boss disposed on the top surface for mounting said curved brush mount to the neck portion of said housing; and a plurality of mounting slots defined in the bottom surface, the mounting slots for insertable mounting of said brush units.

3. The curved-head electric toothbrush according to claim 2, wherein said mounting boss comprises a central drive bore and a pair of spaced stabilizing pegs extending from the mounting boss, the drive bore being disposed between the stabilizing pegs.

4. The curved-head electric toothbrush according to claim 3, wherein:
   each of said brush units comprises a spur gear having an axially extending mounting shaft and a pair of spaced mounting bores, the mounting shaft being insertably mounted into the slots in said curved brush mount;
   each of said brush units comprises a brush mounted to the spur gear, the brush having a mounting collar and a pair of spaced mounting pegs extending from one side of the mounting collar, the mounting pegs being insertably mounted into the mounting bores of the spur gear; and
   each of the brushes has a plurality of curved, outer bristles extending from the to mounting collar opposite the pegs, the outer bristles forming a spherical cage, the brushes further having a plurality of straight, inner bristles disposed inside the outer bristles, the inner bristles having a shorter length than the outer bristles.

5. The curved-head electric toothbrush according to claim 4, wherein each of said spur gears comprises sets of gear teeth at diametrically opposite sectors of said spur gear and smooth sectors devoid of teeth extending between the sets of gear teeth.

6. The curved-head electric toothbrush according to claim 4, wherein the mounting shaft of at least one of said spur gears comprises a notched extension having a semi-circular cross section.

7. The curved-head electric toothbrush according to claim 6, wherein said drive assembly comprises:
   an electric motor having a pinion, the pinion rotating about an axis;
   a motor bracket for securely holding the motor in the housing;
   a crown gear operatively connected to the pinion, the crown gear being rotatable about an axis perpendicular to the rotation axis of the pinion, the crown gear having an eccentric drive boss;
   an elongated transmission arm having one end rotatably mounted to the eccentric drive boss and an opposite end;
   an elongate transmission shaft having one end rotatably attached to the opposite end of the transmission arm, the transmission shaft having an opposite end;
   a crank arm having one end rotatably attached to the opposite end of the elongate transmission shaft, the crank arm having an opposite end; and
   a cam rotatably mounted to the neck portion of said housing, the cam having a first side having an eccentric peg extending therefrom, the eccentric peg being rotatably attached to the opposite end of the crank aim, the can having a second side having a camshaft axially extending therefrom opposite the peg, the camshaft engaging the mounting shaft of the spur gear of said drive brush unit to rotate the same;

wherein rotation of the crown gear eccentrically reciprocates the transmission arm and the transmission shaft, causing the crank arm to rotate the camshaft.

8. The curved-head electric toothbrush according to claim 7, wherein the teeth of the spur gears of adjacent pairs of said brush units mesh so that rotation of said drive brush unit causes adjacent brush units to rotate, adjacent pairs of said brush units rotating in opposite directions.

9. The curved-head electric toothbrush according to claim 7, wherein said curved brush mount is substantially U-shaped, having a pair of legs joined by a bight, the mounting boss on the top surface of said brush mount being centrally disposed on the bight, the legs of said U-shaped brush mount extending opposite the neck portion of said housing.

* * * * *